United States Patent
Tejidor et al.

(10) Patent No.: US 12,265,014 B2
(45) Date of Patent: Apr. 1, 2025

(54) SYSTEMS AND METHODS FOR EVALUATING IMMUNE RESPONSE TO INFECTION VIA MONITORING CELL GRANULARITY PARAMETER OF CELLS

(71) Applicant: Beckman Coulter, Inc., Brea, CA (US)

(72) Inventors: Liliana Tejidor, Coral Gables, FL (US); Robert T. Magari, Cooper City, FL (US); Diana Careaga, Miami, FL (US); Sanghyuk Shin, Carlsbad, CA (US)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 18/367,705

(22) Filed: Sep. 13, 2023

(65) Prior Publication Data
US 2024/0053253 A1    Feb. 15, 2024

Related U.S. Application Data

(62) Division of application No. 16/925,937, filed on Jul. 10, 2020, now Pat. No. 11,796,447.
(Continued)

(51) Int. Cl.
*G01N 15/14* (2024.01)
*G01N 33/80* (2006.01)
(Continued)

(52) U.S. Cl.
CPC ......... *G01N 15/1459* (2013.01); *G01N 33/80* (2013.01); *G01N 2015/012* (2024.01);
(Continued)

(58) Field of Classification Search
CPC ......... G01N 15/1459; G01N 2015/012; G01N 2015/1006; G01N 2800/26;
(Continued)

(56) References Cited

U.S. PATENT DOCUMENTS

| | | |
|---|---|---|
| 5,125,737 A | 7/1992 | Rodriquez et al. |
| 5,341,291 A | 8/1994 | Roizen, III et al. |

(Continued)

FOREIGN PATENT DOCUMENTS

| | | |
|---|---|---|
| CN | 102033035 B | 11/2013 |
| EP | 1021701 | 7/2000 |

(Continued)

OTHER PUBLICATIONS

Abiramalatha, T., et al. "Utility of neutrophil volume conductivity scatter (VCS) parameter changes as sepsis screen in Neonates." Journal of Perinatoloty 36.9 (2016): 733-738.
(Continued)

*Primary Examiner* — Michael P LaPage
(74) *Attorney, Agent, or Firm* — FROST BROWN TODD LLP

(57) ABSTRACT

Systems and methods for characterizing immune response to infection using cellular analysis, such as a hematological cellular analyzer. In some instances, the immune response may be characterized as normal or abnormal based on one or more blood cell population parameters. In some instances, abnormal characterization may be used to identify patients with sepsis or at elevated risk of developing sepsis.

10 Claims, 6 Drawing Sheets

Related U.S. Application Data

(60) Provisional application No. 62/873,575, filed on Jul. 12, 2019.

(51) Int. Cl.
  *G01N 15/01* (2024.01)
  *G01N 15/10* (2006.01)
  *G01N 33/48* (2006.01)

(52) U.S. Cl.
  CPC ..... *G01N 2015/1006* (2013.01); *G01N 33/48* (2013.01); *G01N 2800/26* (2013.01); *G01N 2800/52* (2013.01)

(58) Field of Classification Search
  CPC ....... G01N 2800/52; G01N 2800/7095; G01N 33/56972; G01N 33/80; G01N 33/56966; G01N 33/48; G01N 35/00584
  See application file for complete search history.

(56) References Cited

U.S. PATENT DOCUMENTS

| | | | |
|---|---|---|---|
| 5,529,933 | A | 6/1996 | Young et al. |
| 6,228,652 | B1 | 5/2001 | Rodriquez et al. |
| 6,509,192 | B1 | 1/2003 | Young |
| 7,109,036 | B2 | 9/2006 | Ortiz et al. |
| 7,135,341 | B2 | 11/2006 | Ortiz et al. |
| 7,176,031 | B2 | 2/2007 | Li et al. |
| 7,195,919 | B2 | 3/2007 | Jacobs et al. |
| 7,285,417 | B2 | 10/2007 | Ortiz et al. |
| 7,390,662 | B2 | 6/2008 | Riley et al. |
| 7,393,688 | B2 | 7/2008 | Ortiz et al. |
| 8,094,299 | B2 | 1/2012 | Wells et al. |
| 8,189,187 | B2 | 5/2012 | Graham et al. |
| 8,221,995 | B2 | 7/2012 | Lee et al. |
| 8,719,053 | B2 | 5/2014 | Showalter et al. |
| 9,939,453 | B2 | 4/2018 | Lu et al. |
| 10,221,453 | B2 | 3/2019 | Shi et al. |
| 2001/0051879 | A1 | 12/2001 | Johnson et al. |
| 2001/0051880 | A1 | 12/2001 | Schurenberg et al. |
| 2003/0105648 | A1 | 6/2003 | Schurenberg et al. |
| 2004/0042471 | A1 | 3/2004 | Yung et al. |
| 2004/0220761 | A1 | 11/2004 | Yundt-Pacheco |
| 2004/0267562 | A1 | 12/2004 | Fuhrer et al. |
| 2005/0022103 | A1 | 1/2005 | Yundt-Pacheco |
| 2005/0159982 | A1 | 7/2005 | Showalter et al. |
| 2008/0186134 | A1 | 8/2008 | Parkhurst et al. |
| 2009/0149724 | A1 | 6/2009 | Mark et al. |
| 2011/0046910 | A1 | 2/2011 | Haas et al. |
| 2011/0076685 | A1 | 3/2011 | Moeller et al. |
| 2011/0166794 | A1 | 7/2011 | Linssen et al. |
| 2012/0109531 | A1 | 5/2012 | Knafel et al. |
| 2012/0109682 | A1 | 5/2012 | Seltzer et al. |
| 2013/0123131 | A1 | 5/2013 | Purvis et al. |
| 2013/0197943 | A1 | 8/2013 | Conlin et al. |
| 2013/0246079 | A1 | 9/2013 | Hoffman et al. |
| 2014/0148350 | A1* | 5/2014 | Spetzler ............. G01N 33/6893 436/501 |
| 2014/0160464 | A1 | 6/2014 | Han |
| 2014/0172321 | A1 | 6/2014 | Han |
| 2015/0338427 | A1 | 11/2015 | Pollack et al. |
| 2016/0168638 | A1 | 6/2016 | Garrett et al. |
| 2016/0356801 | A1 | 12/2016 | Glavina et al. |
| 2017/0248508 | A1 | 8/2017 | Ward et al. |
| 2017/0285624 | A1 | 10/2017 | Lesher |
| 2017/0356921 | A1 | 12/2017 | Van Roosmalen et al. |
| 2018/0305758 | A1 | 10/2018 | Shi et al. |
| 2019/0128906 | A1 | 5/2019 | Ramirez et al. |
| 2019/0170749 | A1* | 6/2019 | Anderson ......... G01N 33/56972 |
| 2019/0324035 | A1 | 10/2019 | Magari et al. |
| 2019/0324036 | A1 | 10/2019 | Xin et al. |
| 2019/0348182 | A1 | 11/2019 | Magari et al. |
| 2019/0383800 | A1 | 12/2019 | Careaga et al. |
| 2020/0243171 | A1 | 7/2020 | Schmidt |
| 2020/0253562 | A1* | 8/2020 | Newberry ................ A61B 5/01 |
| 2020/0253564 | A1 | 8/2020 | Barak et al. |
| 2021/0007675 | A1 | 1/2021 | Tejidor et al. |
| 2021/0010924 | A1 | 1/2021 | Tejidor et al. |
| 2021/0011005 | A1 | 1/2021 | Tejidor et al. |
| 2021/0059597 | A1* | 3/2021 | Chung ................ A61B 5/6833 |
| 2021/0303818 | A1 | 9/2021 | Randolph et al. |
| 2023/0005566 | A1 | 1/2023 | Xin et al. |

FOREIGN PATENT DOCUMENTS

| | | |
|---|---|---|
| EP | 1718966 | 11/2006 |
| JP | 2012-529033 A | 11/2012 |
| KR | 20150036329 A | 4/2015 |
| KR | 20150091049 A | 8/2015 |
| WO | WO 2004/044556 A2 | 5/2004 |
| WO | WO 2012/139047 A2 | 10/2012 |
| WO | WO 2014/028534 A2 | 2/2014 |
| WO | WO 2014/084930 A1 | 6/2014 |
| WO | WO 2014/154810 A1 | 10/2014 |
| WO | WO 2017/132132 A1 | 8/2017 |

OTHER PUBLICATIONS

Aird, William C., "The Hematologic System as a Marker of Organ Dysfunction in Sepsis", Mayo Clin Proc., Jul. 2003;78:869-881, 2003 Mayo Foundation for Medical Education and Research.

Anonymous, "Multiple Logistic Regression Analysis", Jan. 17, 2013, retrieved from http://sphweb.bumc.cu.edu/otlt/MPH-Modules/8S/8S704_Multivariable/8S704_Multivariables8.html.

Beckman Coulter, "Coulter® 3-D VCS Technology," from <http://www.cyto.purdue.edu/cdroms/cyto2/6/coulter/ ss000125.htnn> (Year: 1996).

Beckman Coulter, Early Sepsis Indicator (ESId) Application for UniCel DxH 900 Series with System Manager Software, PN C26693AC (Jun. 2019), <https://www.beckmancoulter.corn/download/file/wsr-308328/C26693AC?type=pdf> (Year: 2019).

Beckman Coulter, Early Sepsis Indicator (ESId) Application Addendum, UniCel DxH 900 Series with System Manager Software Coulter Cellular Analysis System, Pn C42014AC (Apr. 2020), <https://www.beckmancoulter.com/download/file/wsr-292218/C42014AC?type=pdf> (Year: 2020).

Beckman Coulter, UniCel DxH 900 Series with System Manager Software, PN B26647AG, <https:// www.beckmancoulter.corn/download/file/wsr-156667/B26647AG?type=pdf> (Year: 2020).

Bhargava, et al. "Elevated mean neutrophil volume+ CRP is a highly sensitive and specific predictor of neonatal sepsis", Letter to the Editor, International Journal of Laboratory Hematology, DOI: 10.1111/iijh.12120, 2013, 4 pages.

"Biomarker" The Pharmaceutical Society of Japan, a pharmaceutical science glossary, 2008, 2 pgs.

Celik, et al., "Automated determination of neutrophil VCS parameters in diagnosis and treatment efficacy of neonatal sepsis", Pediatric Research, vol. 71, No. 1, Jan. 2012, pp. 121-125.

Cembrowski, George S., B. Smith, and D. Tung. "Rationale for using insensitive quality control rules for today's hematology analyzers." *International Journal of Laboratory Hematology* 32.6p2 (2010): 606-615.

Chaves, et al. "Neutrophil Volume Distribution Width: A New Automated Hematologic Parameter for Acute Infection", Arch Pathol Lab Med, vol. 130. Mar. 2006, pp. 378-380.

Chaves, et al. Quantitative Determination of Neutrophil VCS Parameters by the Coulter Automated Hematology Analyzer: New and Reliable Indicators for Acute Bacterial Infection. American Journal Clinical Pathology, 2005, 124:440-444.

Chen, Hong-Jhang, et al. "Study on Yang-Xi Using Body Constitution Questionnaire and Blood Variables in healthy Volunteer." Evidence—Based Complementary and Alternative Medicine 2016 (2016).

Cho, et al., "Biomarkers of Sepsis", Infection & Chemotherapy, Feb. 2014; 46:1-12.

Crouser, et al., "Improved Early Detection of Sepsis in the ED with a Novel Monocyte Distribution Width Biomarker", 152#3 Chest, Sep. 2017, pp. 518-526.

(56) References Cited

OTHER PUBLICATIONS

Dellinger, et al. "Surviving Sepsis Campaign: International Guidelines for Management of Severe Sepsis and Septic Shock, 2012", Intensive Care Medicine, 2013, 39:164-228.

Dilmoula, et al., "Volume, Conductivity and Scatter Properties of Leukocytes (VCS Technology) in Detecting Sepsis in Critically Ill Adult Patients", Blood (ASH annual Meeting Abstracts) 2011; 118: Abstract 4729, 3 pages.

Early Sepsis Indicator Application Addendum UniCel DxH 900 Coulter Cellular Analysis System, Beckman Coulter, published Version: v1, Available online at: https://www.analis.be/site/objects/media/0/0/8/1/9/0081990_media/medial.pdf, Apr. 26, 2018, 38 pages.

Ferrer, et al., "Emperic Antibiotic Treatment Reduces Mortality in Severe Sepsis and Septic Shock from the First Hour: Results from a Guideline-Based Performance Improvement Program", Critical Care Medicine, Aug. 2014, vol. 42, No. 8, pp. 1749-1755.

FDA 510(k) Substantial Equivalence Determination Decision Summary, <https://www.accessdata.fda.gov/cdrh_docs/reviews/K181599.pdf> (Year: 2018).

Gaieski, et al., "Impact of time to antibiotics on survival in patients with severe sepsis or septic shock in whom early goal-directed therapy was initiated in the emergency department", Critical Care Medicine, 2010, vol. 38, No. 4, pp. 1045-1053.

Garnacho-Montero, et al., "Impact of adequate empirical antibiotic therapy on the outcome of patients admitted to the intensive care unit with sepsis", Critical Care Medicine, 2003;31 :2742-51.

Gea-Banecloche, et al. "Sepsis associated with immunosuppressive medications: An evidence-based review" Critical Care Medicine 2004; 32:S578-S590.

Glickman, et al., Disease Progression in Hemodynamically Stable Patients Presenting to the Emergency Department with Sepsis. Academic Emergency Medicine, vol. 17, Issue 4, Apr. 2, 2010, pp. 383-390.

Goyette, et al., "Hematologic changes in sepsis and their therapeutic implications," Seminars in Respiratory and Critical Care Medicine, vol. 25, No. 6, pp. 645-659 (2004).

Hou, et al., Viral infection triggers rapid differentiation of human blood monocytes into dendritic cells, Blood, Mar. 29, 2012, vol. 119, No. 12, pp. 3128-3132.

Kaukonen, et al., "Systemic Inflammatory Response Syndrome Criteria in Defining Severe Sepsis," New England Journal of Medicine, 372: 1629-38, Apr. 23, 2015, (doi:610.1056/NEJMoal415236).

Lee, et al., "Mean cell vols. of neutrophils and monocytes are promising markers of sepsis in elderly patients", Blood Research, vol. 48, No. 3, Sep. 2013, 5 pages.

Levy, et al., "2001 SCCM/ESICM/ACCP/ATS/SIS Sepsis Definitions Conference", Critical Care Medicine, Mar. 28, 2003, 29: 530-538.

Liu, et al., "Hospital Deaths in Patients with Sepsis from 2 Independent Cohorts", JAMA Jul. 2, 2014; 312: 90-92.

Mardi, et al., Mean cell volume of neutrophils and monocytes compared with C-reactive protein, interleukin-6 and white blood cell count for prediction of sepsis and nonsystemic bacterial infections, accepted for publication, Sep. 23, 2009, International Journal of Laboratory Hematology 2010;32:410-418.

Nachimuthu, Senthil K., and Peter J. Haug. "Early detection of sepsis in the emergency department using Dynamic Bayesian Networks." *AMIA Annual Symposium Proceedings*. vol. 2012. American Medical Informatics Association, 2012.

Petrak, Russel M., et al. "The value of an infectious diseases specialist." *Clinical infectious diseases* 36.8 (2003): 1013-1017.

Park, et al., "Screening of sepsis using leukocyte cell population data from the Coulter automatic blood cell analyzer DxH800", International Journal of Laboratory Hematology, Dec. 6, 2010, 9 pages.

Raimondi, et al., "Automated Determination of Neutrophil Volume as Screening Test for Late-Onset Sepsis in Very Low Birth Infants", Pediatric Infectious Disease Journal, Feb. 2010; 29:288-89.

"Red Blood Cell Distribution With (RDW): Definition and Calculation—LabCE.com, Laboratory Continuing Education," Nov. 2012, downloaded Aug. 22, 2019 from: https://labce.com/spg579122_red_blood_cell_distribution_width_rdw_definition_a.aspx, 1 pg.

Seymour, et al. "Severe Sepsis in Pre-Hospital Emergency Care: Analysis of Incidence, Care, and Outcome", American Journal of Respiratory Critical Care Medicine, Dec. 15, 2012; 186:1264-71.

Shalova, et al., "Human Monocytes Undergo Functional Reprogramming during Sepsis Mediated by Hypozia-Inducible Factor-1a", Immunity, Mar. 17, 2015; 42:484-98.

Singer, et al., "The Third International Consensus Definitions for Sepsis and Septic Shock (Sepsis-3)," JAMA, 10 315(8): 801-810, Feb. 23, 2016.

Skibsted, et al., "Bench-to-bedside review: Future novel diagnostics for sepsis—a systems biology approach", Critical Care Oct. 4, 2013; 17:231, 15 pages.

Sukhacheva, et al., "The Role of Monocytes in the Progression of Sepsis," Beckman Coulter, 2018, downloaded Aug. 22, 2019 from: media.beckmancoulter.com/-/media/diagnostics/products/hematology/early-sepsis-indicator/docs/role-of-monocytes-for-progression-of-sepsis-en.pdf, 12 pgs.

Torio, et al., "National Inpatient Hospital Costs: The Most Expensive Conditions by Payer, 2011", H-Cup US, Aug. 2013, 8 pages, retrieved from: https://www.hcup-us.ahrq.gov/reports/statbriefs/sb160.jsp.

"UniCel DxH 800—Coulter Cellular Analysis System", Available online at: https://www.udh.med.sa/advices/DxH_operator_Manual.pdf, Aug. 5, 2017, 54 pages.

Vis, et al., "Verification and Quality Control of Routine Hematology Analyzers", International Journal of Laboratory Hematology, vol. 38, No. 1, May 9, 2016, pp. 100-109.

Warner, "Tips for evaluating a peripheral blood smear for possible sepsis," Jan. 15, 2013, 3 pages, available at laboratorian.advanceweb.com/signs-of-sepsis/.

Zhou, et al., "VCS parameters of neutrophils, monocytes and lymphocytes may indicate local bacterial infection in cancer patients who accepted cytotoxic chemotherapeutics," Eur J Clin Microbiol Infect Dis, 2016, 35:41-48, 8 pgs.

Zonneveld, R., et al., "Analyzing Neutrophil Morphology, Mechanics, and Motility in Sepsis: Options and Challenges for Novel Bedside Technologies," Crit Care Med, 2016, 44(1):218-228, 11 pgs.

Chinese Office Action dated Feb. 16, 2023 for Application No. 201880076679.9, 3 pages.

European Examination Report dated Oct. 15, 2020 for Application No. EP 17704357.7, 10 pgs.

European Examination Report dated Jul. 12, 2022, for Application No. 18845383.1, 13 pages.

European Examination Report dated Jan. 25, 2023 for Application No. EP 19728159., 5 pages.

Indian Office Action dated Jun. 25, 2021, for Application No. 201817031635, 7 pages.

International Search Report and Written Opinion dated Apr. 20, 2017 for International Application No. PCT/US2017/014708, 16 pages.

International Search Report and Written Opinion dated May 4, 2018 for International Application No. PCT/US2018/020087, 13 pages.

International Search Report and Written Opinion dated Mar. 26, 2019 for International Application No. PCT/US2018/057645, 16 pages.

International Search Report and Written Opinion dated Sep. 4, 2019 for International Application No. PCT/US2019/028486, 11 pgs.

International Search Report and Written Opinion dated Aug. 2, 2019 for International Application No. PCT/US2019/028487, 7 pages.

International Search Report and Written Opinion dated Aug. 23, 2019 for International Application No. PCT/US2019/028488, 10 pgs.

International Search Report and Written Opinion dated Aug. 20, 2019 for International Application No. PCT/US2019/031151, 9 pages.

International Search Report and Written Opinion dated Oct. 20, 2020 for International Application No. PCT/US2020/041535, 12 pgs.

(56) References Cited

OTHER PUBLICATIONS

International Search Report and Written Opinion dated Oct. 8, 2020 for International Application No. PCT/US2020/041548, 10 pgs.
International Search Report and Written Opinion dated Oct. 5, 2020 for International Application No. PCT/US2020/041541, 10 pgs.
Japanese Office Action, Notice of Reasons for Refusal, dated Jan. 30, 2023 for JP 2022-076469, 1 page.
Japanese Office Action, Notice of Reasons for Refusal, dated Oct. 29, 2020 JP 2018-538892, 27 pgs.
Japanese Notification of Reasons for Refusal dated Feb. 4, 2022, for Application No. 2021-012832, 4 pages.
Japanese Notification of Reasons for Refusal dated Jun. 17, 2022, for Application No. 2021-012832, 2 pages.
Korean Office Action dated Mar. 20, 2023 for KR 10-2022-7020710, 23 pages.
Korean Office Action dated Aug. 27, 2021, for Application No. 10-2018-7024386, 27 pages.
US Office Action, Final Rejection dated Nov. 29, 2022 for U.S. Appl. No. 16/170,389, 22 pages.
US Office Action, Final Rejection dated Nov. 28, 2022 for U.S. Appl. No. 16/390,597, 9 pages.
US Office Action, Non-Final Rejection, dated Jan. 19, 2023 for U.S. Appl. No. 16/925,943, 20 pages.
US Office Action, Non-Final Rejection, dated Jan. 19, 2023 for U.S. Appl. No. 17/391,599, 34 pages.
US Office Action, Final Rejection, dated Mar. 3, 2023 for U.S. Appl. No. 16/925,933, 11 pages.
US Office Action, Non-Final Rejection, dated Mar. 14, 2023 for U.S. Appl. No. 16/170,389, 9 pages.
US Office Action, Restriction Requirement, dated Apr. 7, 2021 for U.S. Appl. No. 15/987,541, 5 pgs.
US Office Action, Non-Final Rejection, dated Jul. 31, 2020 for U.S. Appl. No. 16/073,757, 23 pgs.
US Office Action, Notice of Allowance, dated Feb. 8, 2021 for U.S. Appl. No. 16/073,757, 20 pgs.
US Non-Final Rejection dated Jul. 9, 2021, for U.S. Appl. No. 15/987,541, 15 pages.
US Final Rejection dated Feb. 17, 2022, for U.S. Appl. No. 15/987,541, 14 pages.
US Notice of Allowance dated Sep. 1, 2022, for U.S. Appl. No. 15/987,541, 8 pages.
US Restriction Requirement dated May 2, 2022, for U.S. Appl. No. 16/170,389, 7 pages.
US Non-Final Rejection dated Aug. 1, 2022, for U.S. Appl. No. 16/170,389, 21 pages.
US Restriction Requirement dated Mar. 14, 2022, for U.S. Appl. No. 16/390,597, 6 pages.
US Non-Final Rejection dated Jun. 13, 2022, for U.S. Appl. No. 16/390,597, 8 pages.
US Non-Final Rejection dated Jul. 2, 2021, for U.S. Appl. No. 16/390,633, 9 pages.
US Non-Final Rejection dated Feb. 25, 2022, for U.S. Appl. No. 16/390,633, 13 pages.
US Final Rejection dated Aug. 9, 2022, for U.S. Appl. No. 16/390,633, 11 pages.
US Non-Final Rejection dated Jul. 9, 2021, for U.S. Appl. No. 16/390,648, 15 pages.
US Final Rejection dated Feb. 17, 2022, for U.S. Appl. No. 16/390,648, 14 pages.
US Notice of Allowance dated Jun. 15, 2022, for U.S. Appl. No. 16/390,648, 7 pages.
US Restriction Requirement dated Jun. 16, 2021, for U.S. Appl. No. 16/488,503, 8 pages.
US Non-Final Rejection dated Nov. 24, 2021, for U.S. Appl. No. 16/488,503, 21 pages.
US Final Rejection dated Aug. 11, 2022, for U.S. Appl. No. 16/488,503, 21 pages.
US Non-Final Rejection dated Jun. 23, 2022, for U.S. Appl. No. 16/925,933, 9 pages.
US Restriction Requirement dated Oct. 5, 2022, for U.S. Appl. No. 16/925,943, 8 pages.
Bruscia, Emanuela M., et al. "Abnormal trafficking and degradation of TLR4 underlie the elevated inflammatory response in cystic fibrosis." *The Journal of Immunology* 186.12 (2011): 6990-6998.
Kirkpatrick, Brian, and Brian J. Miller. "Inflammation and schizophrenia." *Schizophrenia bulletin* 39.6 (2013): 1174-1179.
Lin, Yaojin, et al. "Synthesizing decision rules from multiple information sources: A neighborhood granulation viewpoint." *International Journal of Machine Learning and Cybernetics* 9 (2018): 1919-1928.
Purohit, Abhishek HL, et al. "Volume conductivity, and scatter parameters as diagnostic aid to bacterial sepsis: A tertiary care experience." *Indian Journal of Pathology and Microbiology* 58.4 (2015): 459-463.
Suresh, Pooja K., et al. "Volume conductivity and scatter parameters as an indicator of acute bacterial infections by the automated haematology analyser." *Journal of clinical and diagnostic research*: JCDR 10.1 (2016): EC01.
European Examination Report dated Jan. 2, 2024, for Application No. 23197126.8, 10 pages.
Japanese Notification of Reasons for Refusal dated Apr. 8, 2024, for Application No. 2022-500896, 6 pages.
Korean Final Office Action dated Oct. 20, 2023, for Application No. 10-2022-7020710, 6 pages.
US Notice of Allowance dated Jan. 24, 2024, for U.S. Appl. No. 16/390,597, 9 pages.
US Non-Final Office Action dated Nov. 3, 2023, for U.S. Appl. No. 16/925,933, 14 pages.
US Notice of Allowance dated Feb. 23, 2024, for U.S. Appl. No. 16/925,933, 8 pages.
US Non-Final Office Action dated Jul. 11, 2023, for U.S. Appl. No. 16/925,943, 31 pages.
US Non-Final Office Action dated Mar. 7, 2024, for U.S. Appl. No. 16/925,943, 40 pages.
US Final Office Action dated Aug. 3, 2023, for U.S. Appl. No. 17/391,599, 32 pages.
US Notice of Allowance dated Apr. 5, 2024, for U.S. Appl. No. 17/391,599, 13 pages.

\* cited by examiner

SYSTEMS AND METHODS FOR EVALUATING IMMUNE RESPONSE TO INFECTION VIA MONITORING CELL GRANULARITY PARAMETER OF CELLS

CROSS-REFERENCE TO RELATED APPLICATIONS

This is a divisional of, and claims the benefit of, U.S. patent application Ser. No. 16/925,937 entitled, "Systems and Methods for Using Cell Granularitry in Evaluating Immune Response to Infection," filed on Jul. 10, 2023, which itself is a non-provisional of, and claims the benefit of, U.S. Provisional Patent Application No. 62/873,575 entitled, "Systems and Methods for Evaluating Immune Response to Infection," filed on Jul. 12, 2019, each of which is hereby incorporated by reference in its entirety.

BACKGROUND

Sepsis is a life-threatening organ dysfunction caused by a dysregulated host response to infection. Sepsis is a global healthcare crisis, affecting over 30 million people worldwide each year. The occurrence of sepsis is increasing at an annual rate of 1.5%, making it a significant global healthcare concern. Sepsis has a high mortality rate, killing more individuals than prostate cancer, breast cancer and HIV/AIDS combined.

In addition to the human toll, sepsis is costly to healthcare organizations. Sepsis-related costs—which may include longer hospital stays, ICU admissions, hospital readmissions, and extensive testing and patient monitoring—surpass $24 billion.

Sepsis is a syndrome defined by a set of signs and symptoms. Although sepsis is associated with infection, there is no single cause of sepsis, which can arise from bacterial, viral or fungal infections. Of course, not all infections result in sepsis, and the etiology of sepsis is not well characterized at this time. Further, there is no known biomarker unique to sepsis. Clinicians may rely on non-specific indicators such as fever, white blood cell counts (WBC), and altered mental state (AMS) to identify patients who might have sepsis. These tests are non-specific in that they are present in a variety of conditions other than sepsis, including some cases of non-septic infections, trauma, burns, cancers, etc. Diagnostic tests, including tests for procalcitonin (PCT) and C-Reactive Protein (CRP) are available, but are not desirably specific or sensitive to sepsis. That is, available diagnostic tests both test positive for patients who are not septic and test negative for patients who are septic or who are developing sepsis, at undesirably high rates.

There remains a need for diagnostic tests which can help a clinician distinguish sepsis from other conditions, including flu, trauma, cancer, and non-septic inflammation.

BRIEF SUMMARY

In some aspects, this disclosure relates to a system for evaluating variation in a cell population parameter. The system may comprise a flowcell with a flow of a liquid containing a plurality of cells through the flowcell. The system may comprise a light source, and one or more sensors for detecting light scatter as cells pass through the flowcell. The one or more sensors may comprise a sensor for detecting upper median angle light scatter (UMALS). The system may comprise a processor for identifying non-nucleated red blood cells (NNRBC) based at least in part on one or more light scatter measurements. The processor may further collect the UMALS sensor measurement or measurements for a plurality of identified NNRBCs. The processor may calculate a standard deviation for the UMALS measurements for the plurality of identified NNRBCs.

According to a first aspect, some embodiments may provide a method for characterizing an inflammatory response to infection. In some embodiments, such a method may comprise flowing a body fluid sample though a flowcell, and irradiating a plurality of cells in the body fluid sample in the flowcell. In some embodiments, such a method may further comprise measuring light scatter from individual cells of the plurality of cells including at least UMALS light scatter. In some embodiments, such a method may further comprise identifying individual cells within the plurality of cells, based at least in part on the light scatter measurements. In some embodiments, such a method may further comprise analyzing the UMALS light scatter measurements as a cell population parameter.

According to a second aspect, in some embodiments such as described in the context of the first aspect the body fluid sample may be whole blood.

According to a third aspect, in some embodiments such as described in the context of any of the first or second aspects, the cell population parameter may be analyzed for cells from the plurality of cells classified as NNRBC.

According to a fourth aspect, in some embodiments such as described in the context of any of the first through third aspects, the cell population parameter may be NNRBC-UMALS-SD.

According to a fifth aspect, in some embodiments such as described in the context of the fourth aspect, the method may comprise comparing the NNRBC-UMALS-SD parameter to an NNRBC-UMALS-SD reference range, wherein the inflammatory response to infection is characterized as abnormal if the NNRBC-UMALS-SD is outside the NNRBC-UMALS-SD reference range.

According to a sixth aspect, in some embodiments such as described in the context of any of the fourth or fifth aspects, the inflammatory response to infection may be characterized as abnormal if the NNRBC-UMALS-SD is less than 43.

According to a seventh aspect, in some embodiments such as described in the context of any of the fourth through sixth aspects, the method may further comprise determining whether the distribution width of measured volumes for a population of monocytes (MDW) within the body fluid sample is within an MDW reference range.

According to an eighth aspect, in some embodiments such as described in the context of the seventh aspect, the method may comprise characterizing the inflammatory response to infection as abnormal if the NNRBC-UMALS-SD is outside the NNRBC-UMALS-SD reference range and the MDW is outside the MDW reference range.

According to a ninth aspect, in some embodiments such as described in the context of the seventh or eighth aspects, the inflammatory response to infection is characterized as abnormal if the NNRBC-UMALS-SD is less than 43 and the distribution width of the volume of monocytes is greater than 19 channels.

According to a tenth aspect, in some embodiments such as described in the context of any of the fourth through eighth aspects, the method may further comprise determining whether a count of white blood cells (WBC) in the body fluid sample is within a normal reference range.

According to an eleventh aspect, in some embodiments such as described in the context of the tenth aspect, the inflammatory response to infection may be characterized as abnormal if the NNRBC-UMALS-SD is less than 43 and the WBC is less than 4,000 cells/mm$^3$ or greater than 12,000 cells/mm$^3$.

According to a twelfth aspect, in some embodiments such as described in the context of the first aspect, the method may comprise determining NNRBC-UMALS-SD, MDW and WBC. In some such embodiments, the method may further comprise comparing each of the NNRBC-UMALS-SD, the MDW, and the WBC to a respective reference range. In some such embodiments, the method may further comprise characterizing the inflammatory response to infection based on a combination of at least the NNRBC-UMALS-SD, the MDW, and the WBC.

According to a thirteenth aspect, in some embodiments such as described in the context of the twelfth aspect, the inflammatory response to infection may be characterized as abnormal if the NNRBC-UMALS-SD is outside the NNRBC-UMALS-SD reference range, the MDW is outside the MDW reference range, and the WBC is outside the WBC reference range.

According to a fourteenth aspect, in some embodiments such as described in the context of any of the twelfth to thirteenth aspects, local decision rules may be applied to characterize the inflammatory response to infection if the NNRBC-UMALS-SD, the MDW and the WBC are not all within or all outside of their respective reference ranges.

According to a fifteenth aspect, in some embodiments a system may be provided that comprises a transducer module for measuring at least UMALS light scatter caused by cells passing through the flowcell of the method described in the context of any of the first through fourteenth aspects. In some such embodiments, the system may comprise a processor configured with instructions on a non-transitory computer readable medium for performing the method described in the context of any of the first through fourteenth aspects.

According to a sixteenth aspect, in some embodiments such as described in the context of the fifteenth aspect, the transducer module may comprise means for measuring RF conductivity wherein the means for measuring RF conductivity is operable to measure RF conductivity of cells passing through the flowcell of the method of any of the first through fourteenth aspects and is also operable to measure RF conductivity of cells passing through a second flowcell comprised by the transducer module.

DETAILED DESCRIPTION

Figure 1:
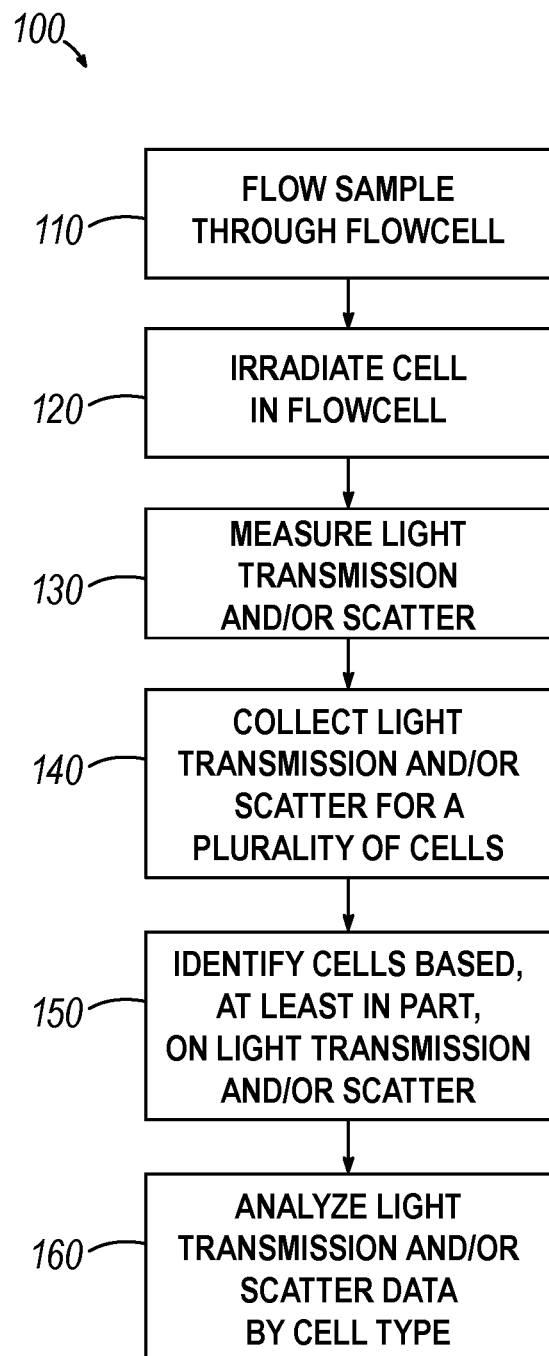
FIG. 1 is a flowchart of an exemplary cellular analysis process in accordance with aspects of this disclosure.

Prior efforts to provide an objective, diagnostic test for sepsis have included hematological cellular analysis. Abnormal White Blood Cell Counts (WBC) are often associated with infection, although they are not specific to sepsis. More recently, evaluation of other cell populations, such as immature granulocytes, has been proposed as a factor to consider in evaluating the likelihood that a patient has or is developing sepsis. Other proposals have included looking at cell population parameters, such as monocyte volume distribution width or neutrophil volume distribution width, as potential indicators of sepsis. These hematological approaches have tended to focus on white blood cells, including monocytes, lymphocytes, and neutrophils, which are known to be involved in the immune response to infection.

Surprisingly, a UMALS light scatter measurement of non-nucleated red blood cells (NNRBC) has been found to be a good predictor of sepsis, either alone or in combination with other blood cell population parameters. In particular, the standard deviation of the UMALS light scatter measurement for a population of NNRBC may be a good predictor of sepsis. UMALS is sometimes associated with cell granularity, so for granulocytes and their progenitors, UMALS would, in hindsight, seem to be a cellular characteristic of reasonable interest. However, NNRBC do not granulate in response to infection, and are typically a heterogenous population due to changes in red blood cell size and morphology as cells age. There was no apparent reason to believe that UMALS measurement of NNRBC would provide insight into the likelihood a patient has or is at risk of developing sepsis, and in particular no reason to believe that changes in the standard deviation for the UMALS measurement of NNRBC would help identify patients with sepsis or developing sepsis.

A blood sample from a patient can be analyzed manually, e.g., by smearing blood on a slide and visually examining the slide. A manual operator can make counts of cells and identify cells by type, e.g., red blood cells, platelets, white blood cells, possibly by using visual aids to facilitate counting and/or sizing cells on the slide. However, it may be desirable to automate the analysis of a blood sample from a patient. Beyond the convenience of having an automated process, an automated or semi-automated cellular analysis system may be able, for example, to count a vastly larger number of cells in a blood sample, or to gather information about individual cells and/or cell populations that would be extremely challenging or impossible for a human to collect at a comparable sample size. These abilities are important to producing sufficient data points for cell population statistics, such as distribution width, that are robust based on sample size.

Cellular analysis systems may use a variety of techniques to identify, count and/or characterize cells. For example, a cellular analysis system may use electrical impedance to determine the volume and quantity of cells passing through an interrogation zone in a flowcell. As another example, a cellular analysis system may use imaging technology to capture optical representations of the cell and analyze the optical representations (which might or might not be human-comprehensible or amenable to conversion to human-comprehensible images) to determine the size and quantity of cells in an interrogation zone, either in a quiescent system or in a flowcell. As yet another example, a cellular analysis system may use flow cytometry to irradiate cells passing through a flowcell and measure the transmission and/or scatter of the light as it passes through the cell. The light scatter may inherently distinguish different cells of different kinds, sizes or characteristics, or the cells may be prepared with markers, such as fluorescent markers, to facilitate the identification, quantification and/or characterization of the cells based on cellular features marked—or unmarked—by the marker. A cellular analysis system may use combinations of these and/or other techniques to count, identify, and/or characterize cells. For example, a cellular analysis system may use a combination of electrical impedance and light scatter to analyze cells in a blood sample. If a combination of techniques is used, the techniques may employ hardware set up in serial progression (e.g., the same sample or aliquot of a sample is passed through multiple, separate interrogation zones), or in parallel progression (e.g., different aliquots of a sample are passed at essentially the same time through multiple, separate interrogation zones), or two or more techniques may be employed at the essentially the same time (e.g., a flow cell may be equipped to measure both electrical impedance and light scatter from the same sample or aliquot of sample in the same flow cell at essentially the same time). In this regard, essentially the same time means that the processes are running in overlapping time intervals for the same sample or different aliquots of the same sample. It is not essential to the practice of the invention that the different techniques be coordinated to occur at precisely the same time or in time intervals of equal duration.

A sample for analysis may be any biological fluid which contains cells. The biological fluid may, for example, be blood. The sample may be whole blood, e.g., blood which has not been processed or modified except for the possible addition of an anticoagulant to prevent the blood from clotting, which would complicate flowing the blood through a flowcell for analysis. The sample may be processed, e.g., by dilution, by concentration, by separation into components (such as plasma, serum, and cells); by pretreatment (e.g., with cytometry markers, with a lyse to rupture/remove certain cell types, with a stain to modify the appearance of one or more cells, etc.), with a sphering agent, or otherwise as may be helpful to prepare the sample for analysis. The blood may be human blood or non-human animal blood. In some circumstances, the sample may be from a non-blood body fluid, such as urine, synovial fluid, saliva, bile, cerebrospinal fluid, amniotic fluid, semen, mucus, sputum, lymph, aqueous humour, tears, vaginal secretions, pleural fluid, pericardial fluid, peritoneal fluid, and the like. As with blood, if non-blood body fluids are sampled, the non-blood body fluids may be processed, e.g., concentrated or the cells otherwise enriched, as by centrifugation, to achieve a desirable cellular concentration or to enrich or modify certain sub-populations of cells for analysis. A possible advantage of evaluating whole blood may be the relatively large number of cells available for analysis in a relatively small sample. A possible advantage of analyzing non-blood body fluids and/or processed blood may be pre-segregation of certain cells of interest and/or a reduction in the number of cells, because of differences in the types and number of cells that normally occur in different body fluids. A lower number of cells may be helpful, for example, for characterizing individual cells.

In some aspects, cells passing through a flowcell are analyzed using light scatter. As shown in FIG. 1, a method 100 for evaluating cell population variations may comprise flowing a sample through a flowcell 110. Cells within the sample flowing through the flowcell may be irradiated 120, as with visible light. The cellular analysis system may comprise one or more sensors which allow the analyzer to measure light transmission and/or scatter 130 as a cell is irradiated in the flowcell. The cellular analysis system may comprise a processor or means for communicating with a remote processor to collect the light transmission and/or scatter for a plurality of cells in the sample 140 as the cells flow through the flowcell. The processor may use an algorithm to identify cells based, at least in part, on light transmission and/or scatter 150. The processor, or a separate processor, may analyze the light transmission and/or scatter data for a particular cell or for a particular cell type population 160 (e.g., monocytes, neutrophils, red blood cells). The analysis could comprise, for example, calculating parameters, such as extrema, ranges, standard deviations, distribution widths, etc. for a particular measure, such as cell volume or light scatter, and/or for a particular cell type, such as monocytes, neutrophils, or NNRBC. For example, the cellular analysis system may calculate the standard deviation of light scatter, or of a particular angle of light scatter, such as UMALS, for cells identified as NNRBC. In some aspects, measurement 130 could involve alternative measurements of cell size and/or granularity, such as image analysis, electrical impedance, radiofrequency (RF) response, flow cytometry with or without markers, alone or in combination or sub-combinations, and with or without light transmission and/or light scatter measures.

Figure 2:
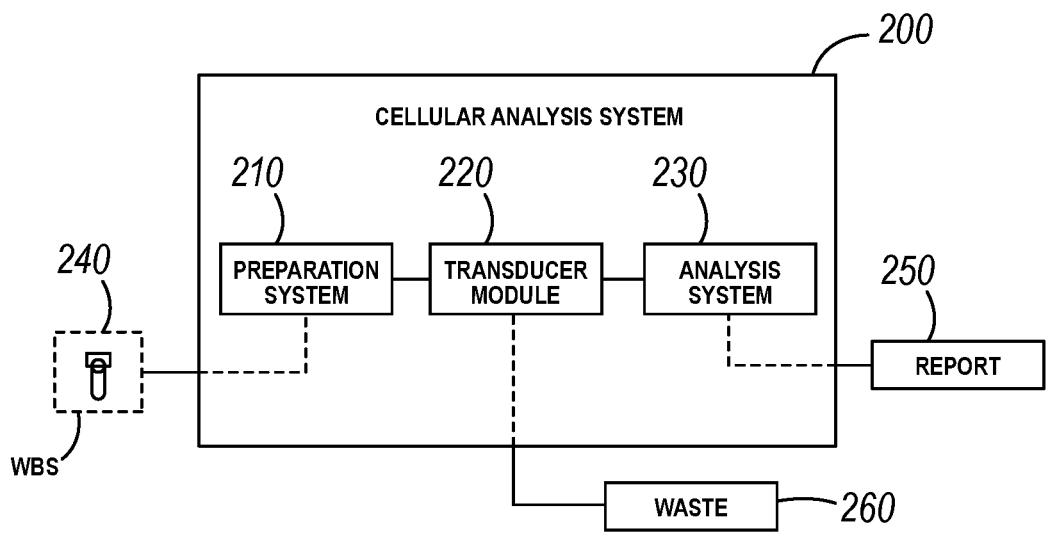
FIG. 2 is a schematic depiction of an exemplary cellular analysis system in accordance with aspects of this disclosure.

FIG. 2 schematically depicts a cellular analysis system 200. As shown here, system 200 includes a preparation system 210, a transducer module 220, and an analysis system 230. While system 200 is described generally with reference to three core system blocks (210, 220, and 230), the skilled artisan readily understands that system 200 may include other system components such as central control processor(s), display system(s), fluidic system(s), temperature control system(s), user-safety control system(s), and the like. In operation, a whole blood sample (WBS) 240 can be presented to the system 200 for analysis. In some instances, WBS 240 is aspirated into system 200. Exemplary aspiration techniques are known to the skilled artisan. After aspiration, WBS 240 can be delivered to a preparation system 210. Preparation system 210 receives WBS 240 and can perform operations involved with preparing WBS 240 for further measurement and analysis. For example, preparation system 210 may separate WBS 240 into one or more predefined aliquots for presentation to transducer module 220. In some aspects, preparation system 210 may make no changes to the composition of WBS 240. Alternately, preparation system 210 may include mixing chambers so that appropriate reagents may be added to one or more of the aliquots. For example, where an aliquot is to be tested for differentiation of white blood cell subset populations, a lysing reagent (e.g. ERYTHROLYSE, a red blood cell lysing buffer) may be added to the aliquot to break up and remove the RBCs. Preparation system 210 may also include temperature control components to control the temperature of the reagents and/or mixing chambers. Appropriate temperature controls can improve the consistency of the operations of preparation system 210, and may facilitate pre-treatment of cells in the sample, e.g., with fluorescent markers, stains, or lyse.

In some instances, one or more predefined aliquots can be transferred from preparation system 210 to transducer module 220. As described in further detail below, transducer module 220 can perform light transmission, and/or light scatter measurements of cells from the WBS passing individually therethrough. Measured light propagation (e.g., light transmission, light scatter) parameters can be provided or transmitted to analysis system 230 for data processing. In some instances, analysis system 230 may include computer processing features and/or one or more modules or components such as those described herein with reference to the system depicted in FIG. 4 and described further below, which can evaluate the measured parameters, identify and enumerate at least one of the blood cellular constituents, and calculate cell population parameters for one or more cell populations within the aliquot. As shown here, cellular analysis system 200 may generate or output a report 250 containing measurements and/or calculated parameters for one or more cell populations within the aliquot, e.g., monocyte volume distribution width, neutrophil volume distribution width, a count or percentage of immature granulocytes, and/or a standard deviation of a UMALS measurement for NNRBC. In some instances, excess biological sample from transducer module 220 can be directed to an external (or alternatively internal) waste system 260. An exemplary cellular analysis system is a Beckman Coulter DxH hematology analyzer, which measures direct current impedance to determine cell volume, conductivity, and light scatter, for cytoplasmic granularity and nuclear structure.

Because there is no known biomarker specific to sepsis (e.g., in the sense that identifying a malarial parasite in a blood cell definitively indicates a malarial infection), there is currently no hematological analysis which can definitively diagnosis sepsis. However, identifying, enumerating and/or characterizing one or more cell populations in a patient samples may provide information which, in combination with clinical signs and symptoms and potentially with other tests or characterization studies, can reliably increase or decrease a clinical suspicion of sepsis or developing sepsis. Notably, because sepsis is a syndrome defined based on clinical symptoms, and because cell population changes may be observed before the clinical symptoms of sepsis, cell population data may help identify patients at high risk of developing sepsis, allowing for prophylactic treatment. This is advantageous because prophylactic treatment often involves the administration of antibiotic, antiviral and/or antifungal medications that pose challenges. For example, overuse of antibiotics in patients who are not septic or developing sepsis can contribute to the development of antimicrobial resistance. Further, some medications may have side effects or trigger adverse events that can be dangerous for a patient who is seriously ill or whose clinical state is declining. Accordingly, a test which can help a clinician develop an informed clinical treatment plan is valuable even if the test itself is not definitively diagnostic. Further, characterizing and/or enumerating cell populations that change during or in advance of a patient developing sepsis may be useful for non-diagnostic purposes, such as research into the etiology or progression of sepsis, or observing cellular responses to infection.

In some aspects, the analysis of a patient sample may cause a clinician to initiate and/or modify a treatment regimen. Treatment regimens may involve administration of one or more medications or therapeutic agents to an individual for the purposes of addressing the patient's condition. Any of a variety of therapeutic modalities can be used for treating an individual identified as having an abnormal NNRBC UMALS standard deviation as discussed herein. Exemplary therapies may include the administration of fluids, vasopressors, antibiotics, antifungals, antivirals, vitamins (including thiamine), minerals, steroids (including corticosteroids), and combinations thereof. In some instances, a patient may be subjected to more or less rigorous monitoring, including being admitting to a hospital for professional observation, based on the analysis of the patient sample. As used herein, an NNRBC UMALS standard deviation is considered normal if it is not associated with a dysfunctional immune response to infection and/or sepsis. An NNRBC UMALS standard deviation is considered abnormal if it is associated with a dysfunctional immune response to infection and/or sepsis.

Figure 3:
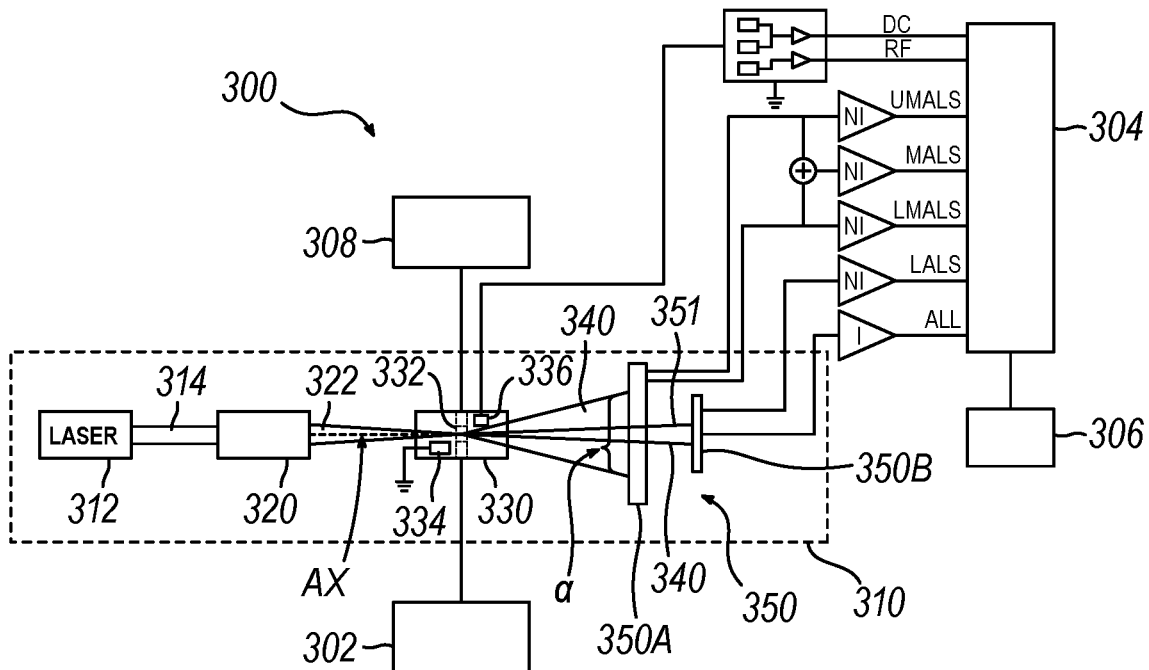
FIG. 3 is an illustration of an exemplary transducer module and associated components in accordance with aspects of this disclosure.

FIG. 3 illustrates in more detail a transducer module and associated components in more detail. As shown here, system 300 includes a transducer module 310 having a light or irradiation source such as a laser 312 emitting a beam 314. The laser 312 can be, for example, a 635 nm, 5 mW, solid-state laser. In some instances, system 300 may include a focus-alignment system 320 that adjusts beam 314 such that a resulting beam 322 is focused and positioned at a cell interrogation zone 332 of a flow cell 330. In some instances, flow cell 330 receives a sample aliquot from a preparation system 302. Various fluidic mechanisms and techniques can be employed for hydrodynamic focusing of the sample aliquot within flow cell 330.

In some instances, the aliquot generally flows through the cell interrogation zone 332 such that its constituents pass through the cell interrogation zone 332 one at a time. In some cases, a system 300 may include a cell interrogation zone or other feature of a transducer module or blood analysis instrument such as those described in U.S. Pat. Nos. 5,125,737; 6,228,652; 7,390,662; 8,094,299; and 8,189,187, the contents of which are incorporated herein by references. For example, a cell interrogation zone 332 may be defined by a square transverse cross-section measuring approximately 50×50 microns, and having a length (measured in the direction of flow) of approximately 65 microns. Flow cell 330 may include an electrode assembly having first and second electrodes 334, 336 for performing DC impedance and/or RF conductivity measurements of the cells passing through cell interrogation zone 332. Signals from electrodes 334, 336 can be transmitted to analysis system 304. The electrode assembly can analyze volume and conductivity characteristics of the cells using low-frequency current and high-frequency current, respectively. For example, low-frequency DC impedance measurements can be used to analyze the volume of each individual cell passing through the cell interrogation zone. High-frequency RF current measurements can be used to determine the conductivity of cells passing through the cell interrogation zone. Because cell walls act as conductors to high frequency current, the high frequency current can be used to detect differences in the insulating properties of the cell components, as the current passes through the cell walls and through each cell interior. High frequency current can be used to characterize nuclear and granular constituents and the chemical composition of the cell interior.

The light source in FIG. 3 has been described as a laser, however, the light source may alternatively or additionally include a xenon lamp, an LED lamp, an incandescent lamp, or any other suitable source of light, including combinations of the same or different kinds of lamps (e.g., multiple LED lamps or at least one LED lamp and at least one xenon lamp). As shown in FIG. 3, for example, incoming beam 322 irradiates the cells passing through cell interrogation zone 332, resulting in light propagation within an angular range a (e.g. scatter, transmission) emanating from the zone 332. Exemplary systems are equipped with sensor assemblies that can detect light within one, two, three, four, five, or more angular ranges within the angular range a, including light associated with an extinction or axial light loss measure. As shown, light propagation 340 can be detected by a light detection assembly 350, optionally having a light scatter detector unit 350A and a light scatter and/or transmission detector unit 350B. In some instances, light scatter detector unit 350A includes a photoactive region or sensor zone for detecting and measuring upper median angle light scatter (UMALS), for example light that is scattered or otherwise propagated at angles relative to a light beam axis within a range from about 20 to about 42 degrees. In some instances, UMALS corresponds to light propagated within an angular range from between about 20 to about 43 degrees, relative to the incoming beam axis which irradiates cells flowing through the interrogation zone. Light scatter detector unit 350A may also include a photoactive region or sensor zone for detecting and measuring lower median angle light scatter (LMALS), for example light that is scattered or otherwise propagated at angles relative to a light beam axis within a range from about 10 to about 20 degrees. In some instances, LMALS corresponds to light propagated within an angular range from between about 9 to about 19 degrees, relative to the incoming beam axis which irradiates cells flowing through the interrogation zone.

A combination of UMALS and LMALS is defined as median angle light scatter (MALS), which may be light scatter or propagation at angles between about 9 degrees and about 43 degrees relative to the incoming beam axis which irradiates cells flowing through the interrogation zone. One of skill in the art will understand that these angles (and the other angles described herein) may vary somewhat based on the configuration of the interrogation, sensing and analysis systems.

As shown in FIG. 3, the light scatter detector unit 350A may include an opening 351 that allows low angle light scatter or propagation 340 to pass beyond light scatter detector unit 350A and thereby reach and be detected by light scatter and transmission detector unit 350B. According to some embodiments, light scatter and transmission detector unit 350B may include a photoactive region or sensor zone for detecting and measuring lower angle light scatter (LALS), for example light that is scattered or propagated at angles relative to an irradiating light beam axis of less than about 5.1 degrees. In some instances, LALS corresponds to light propagated at an angle of less than about 9 degrees, relative to the incoming beam axis which irradiates cells flowing through the interrogation zone. In some instances, LALS corresponds to light propagated at an angle of less than about 10 degrees, relative to the incoming beam axis which irradiates cells flowing through the interrogation zone. In some instances, LALS corresponds to light propagated at an angle of about 1.9 degrees±0.5 degrees, relative to the incoming beam axis which irradiates cells flowing through the interrogation zone. In some instances, LALS corresponds to light propagated at an angle of about 3.0 degrees±0.5 degrees, relative to the incoming beam axis which irradiates cells flowing through the interrogation zone. In some instances, LALS corresponds to light propagated at an angle of about 3.7 degrees±0.5 degrees, relative to the incoming beam axis which irradiates cells flowing through the interrogation zone. In some instances, LALS corresponds to light propagated at an angle of about 5.1 degrees±0.5 degrees, relative to the incoming beam axis which irradiates cells flowing through the interrogation zone. In some instances, LALS corresponds to light propagated at an angle of about 7.0 degrees±0.5 degrees, relative to the incoming beam axis which irradiates cells flowing through the interrogation zone. In each instance, LALS may correspond to light propagated an angle of about 1.0 degrees or more. That is, LALs may correspond to light propagated at angles between about 1.0 degrees and about 1.9 degrees; between about 1.0 degrees and about 3.0 degrees; between about 1.0 degrees and about 3.7 degrees; between about 1.0 degrees and about 5.1 degrees, between about 1.0 degrees and about 7.0 degrees, between about 1.0 degrees and about 9.0 degrees; or between about 1.0 degrees and about 10.0 degrees.

According to some embodiments, light scatter and transmission detector unit 350B may include a photoactive region or sensor zone for detecting and measuring light transmitted axially through the cells, or propagated from the irradiated cells, at an angle of about 0 degrees relative to the incoming light beam axis. In some cases, the photoactive region or sensor zone may detect and measure light propagated axially from cells at angles of less than about 1 degree relative to the incoming light beam axis. In some cases, the photoactive region or sensor zone may detect and measure light propagated axially from cells at angles of less than about 0.5 degrees relative to the incoming light beam axis less. Such axially transmitted or propagated light measurements correspond to axial light loss (ALL or AL2). As noted in previously incorporated U.S. Pat. No. 7,390,662, when light interacts with a particle, some of the incident light changes direction through the scattering process (i.e. light scatter) and part of the light is absorbed by the particles. Both of these processes remove energy from the incident beam. When viewed along the incident axis of the beam, the light loss can be referred to as forward extinction or axial light loss. Additional aspects of axial light loss measurement techniques are described in U.S. Pat. No. 7,390,662 at column 5, line 58 to column 6, line 4.

As such, the cellular analysis system 300 provides means for obtaining light propagation measurements, including light scatter and/or light transmission, for light emanating from the irradiated cells of the biological sample at any of a variety of angles or within any of a variety of angular ranges, including ALL and multiple distinct light scatter or propagation angles. For example, light detection assembly 350, including appropriate circuitry and/or processing units, provides a means for detecting and measuring UMALS, LMALS, LALS, MALS, and ALL.

Wires or other transmission or connectivity mechanisms can transmit signals from the electrode assembly (e.g. electrodes 334, 336), light scatter detector unit 350A, and/or light scatter and transmission detector unit 350B to analysis system 304 for processing. For example, measured DC impedance, RF conductivity, light transmission, and/or light scatter parameters can be provided or transmitted to analysis system 304 for data processing. In some instances, analysis system 304 may include computer processing features and/or one or more modules or components such as those described herein with reference to the system depicted in FIG. 4, which can evaluate the measured parameters, identify and enumerate biological sample constituents, and correlate a subset of data characterizing elements of the biological sample with one or more features or parameters of interest. As shown here, cellular analysis system 300 may generate or output a report 306 presenting measurements made or parameters calculated for the sample, such as WBC, MDW, or UMALS standard deviation for NNRBC. In some instances, excess biological sample from transducer module 310 can be directed to an external (or alternatively internal) waste system 308. In some instances, a cellular analysis system 300 may include one or more features of a transducer module or blood analysis instrument such as those described in previously incorporated U.S. Pat. Nos. 5,125,737; 6,228,652; 8,094,299; and 8,189,187.

Figure 4:
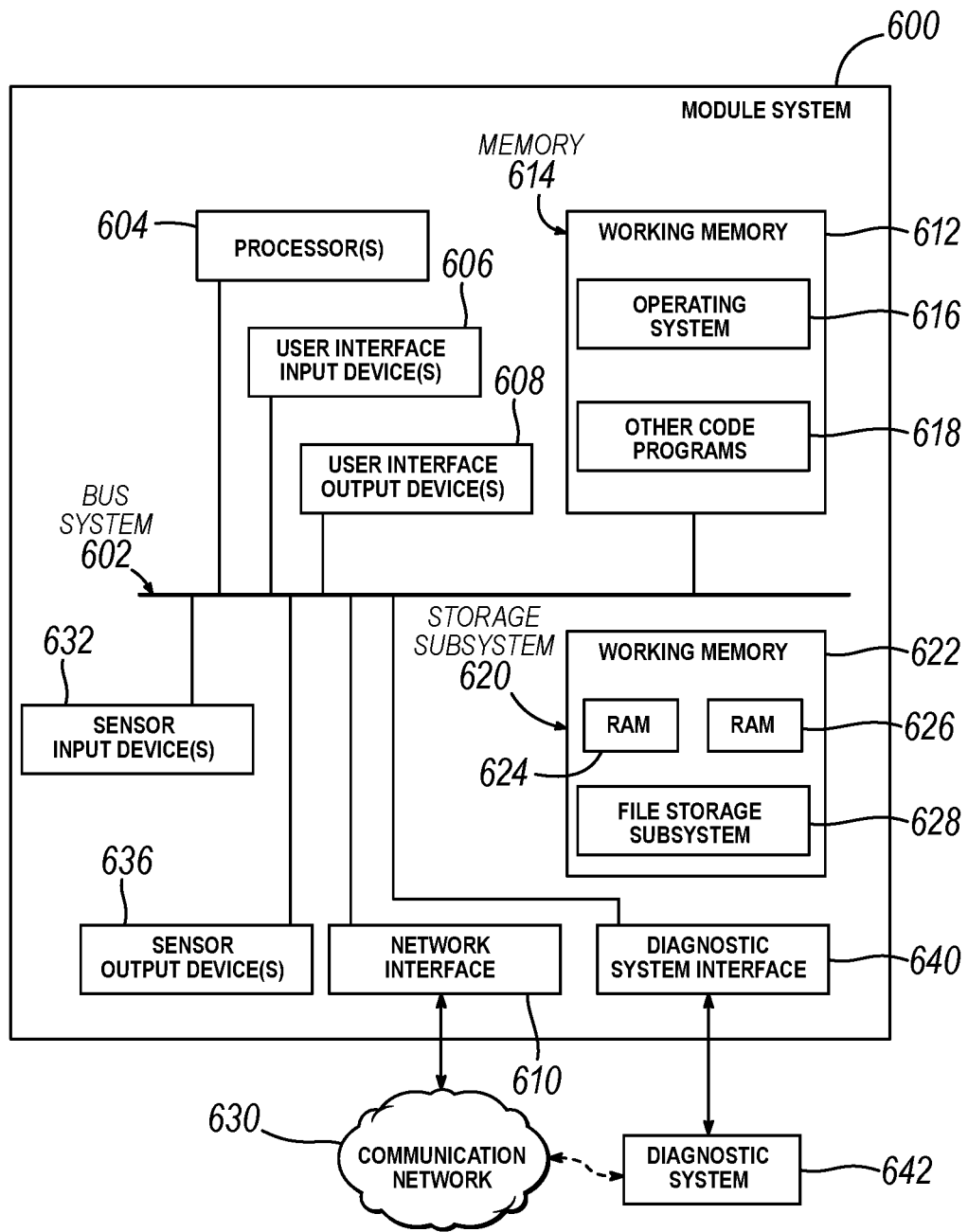
FIG. 4 is a simplified block diagram of an exemplary module system in accordance with aspects of this disclosure.

FIG. 4 is a simplified block diagram of an exemplary module system that broadly illustrates how individual system elements for a module system 600 may be implemented in a separated or more integrated manner. Module system 600 may be part of or in connectivity with a cellular analysis system. Module system 600 is well suited for producing data or receiving input related to a cellular analysis. In some instances, module system 600 includes hardware elements that are electrically coupled via a bus subsystem 602, including one or more processors 604, one or more input devices 606 such as user interface input devices, and/or one or more output devices 608 such as user interface output devices. In some instances, system 600 includes a network interface 610, and/or a diagnostic system interface 640 that can receive signals from and/or transmit signals to a diagnostic system 642. In some instances, system 600 includes software elements, for example shown here as being currently located within a working memory 612 of a memory 614, an operating system 616, and/or other code 618, such as a program configured to implement one or more aspects of the techniques disclosed herein. Memory 614 may be non-transitory and/or embodied in tangible media, such as hardware.

In some embodiments, module system 600 may include a storage subsystem 620 that can store the basic programming and data constructs that provide the functionality of the various techniques disclosed herein. For example, software modules implementing the functionality of method aspects, as described herein, may be stored in storage subsystem 620. These software modules may be executed by the one or more processors 604. In a distributed environment, the software modules may be stored on a plurality of computer systems and executed by processors of the plurality of computer systems. Storage subsystem 620 can include memory subsystem 622 and file storage subsystem 628. Memory subsystem 622 may include a number of memories including a main random access memory (RAM) 626 for storage of instructions and data during program execution and a read only memory (ROM) 624 in which fixed instructions are stored. File storage subsystem 628 can provide persistent (non-volatile) storage for program and data files, and may include tangible storage media which may optionally embody patient, treatment, assessment, or other data. File storage subsystem 628 may include a hard disk drive, a floppy disk drive along with associated removable media, a Compact Digital Read Only Memory (CD-ROM) drive, an optical drive, DVD, CD-R, CD RW, solid-state removable memory, other removable media cartridges or disks, and the like. One or more or all of the drives may be located at remote locations on other connected computers at other sites coupled to module system 600. In some instances, systems may include a computer-readable storage medium or other tangible storage medium that stores one or more sequences of instructions which, when executed by one or more processors, can cause the one or more processors to perform any aspect of the techniques or methods disclosed herein. One or more modules implementing the functionality of the techniques disclosed herein may be stored by file storage subsystem 628. In some embodiments, the software or code will provide protocol to allow the module system 600 to communicate with communication network 630. Optionally, such communications may include dial-up or internet connection communications.

System 600 can be configured to carry out various aspects of methods of the present disclosure. For example, processor component or module 604 can be a microprocessor control module configured to receive cellular parameter signals from a sensor input device or module 632, from a user interface input device or module 606, and/or from a diagnostic system 642, optionally via a diagnostic system interface 640 and/or a network interface 610 and a communication network 630. In some instances, sensor input device(s) may include or be part of a cellular analysis system that is equipped to obtain multiple light angle detection parameters, such as in a Beckman Coulter DxH™ hematology analyzer. In some instances, user interface input device(s) 606 and/or network interface 610 may be configured to receive cellular parameter signals generated by a cellular analysis system that is equipped to obtain multiple light angle detection parameters, such as a Beckman Coulter DxH™ Hematology Analyzer. In some instances, diagnostic system 642 may include or be part of a cellular analysis system that is equipped to obtain multiple light angle detection parameters, such as a Beckman Coulter DxH™ Hematology Analyzer.

Processor component or module 604 can also be configured to transmit cellular parameter signals, optionally processed according to any of the techniques disclosed herein or known to one of skill in the art, to sensor output device or module 636, to user interface output device or module 608, to network interface device or module 610, to diagnostic system interface 640, or any combination thereof. Each of the devices or modules according to embodiments of the present disclosure can include one or more software modules on a computer readable medium that is processed by a processor, or hardware modules, or any combination thereof. Any of a variety of commonly used platforms, such as Windows, MacIntosh, and Unix, along with any of a variety of commonly used programming languages, may be used to implement embodiments of the present disclosure.

User interface input devices 606 may include, for example, a touchpad, a keyboard, pointing devices such as a mouse, a trackball, a graphics tablet, a scanner, a joystick, a touchscreen incorporated into a display, audio input devices such as voice recognition systems, microphones, and other types of input devices. User input devices 606 may also download a computer executable code from a tangible storage media or from communication network 630, the code embodying any of the methods or aspects thereof disclosed herein. It will be appreciated that terminal software may be updated from time to time and downloaded to the terminal as appropriate. In general, use of the term "input device" is intended to include a variety of conventional and proprietary devices and ways to input information into module system 600.

User interface output devices 606 may include, for example, a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from module system 600 to a user. In some instances, a cellular analysis system may not directly include a user interface output device, instead transferring data to a network, computer processor, or computer-readable non-transitory storage medium, with data display for a human user occurring in connection with that device or with devices to which the data from the cellular analysis system is further transferred after the initial transfer. If data is transferred from the analyzer without display, the data transferred may be raw sensor data or processed data or a combination of raw and processed data.

Bus subsystem 602 provides a mechanism for letting the various components and subsystems of module system 600 communicate with each other as intended or desired. The various subsystems and components of module system 600 need not be at the same physical location but may be distributed at various locations within a distributed network. Although bus subsystem 602 is shown schematically as a single bus, alternate embodiments of the bus subsystem may utilize multiple busses.

Network interface 610 can provide an interface to an outside network 630 or other devices. Outside communication network 630 can be configured to effect communications as needed or desired with other systems. It can thus receive an electronic packet from module system 600 and transmit any information as needed or desired back to module system 600. As depicted here, communication network 630 and/or diagnostic system interface 642 may transmit information to or receive information from a diagnostic system 642 that is equipped to obtain multiple light angle detection parameters, such as such as a Beckman Coulter DxH™ Cellular Analysis System. As non-limiting examples, outside communication network 630 may be used to transmit data between a cellular analysis system and a research database, a laboratory information system (LIS), an electronic medical record (EMR), and the like. In some instances, the communication may be one-way, with information flowing from the cellular analysis system to other systems. In some instances, the communication may be one-way with information (such as orders for specific measurements to be made or population parameters to be calculated) flowing from an external system, which may be remote or physically proximate to the cellular analysis system, to the cellular analysis system. In some instances, the communication may be two-way. In some instances, the information communicated to the cellular analysis system by an external system may include patient information useful in evaluating the significance of cellular measurements. For example, some reference ranges for hematology parameters may differ for pediatric populations or specific patient sub-populations relative to a general adult population, and the cellular analysis system may consider patient information when determining whether to flag analytical results for further review.

In addition to providing such infrastructure communications links internal to the system, the communications network system 630 may also provide a connection to other networks such as the internet and may comprise a wired, wireless, modem, and/or other type of interfacing connection.

It will be apparent to the skilled artisan that substantial variations may be used in accordance with specific requirements. For example, customized hardware might also be used and/or particular elements might be implemented in hardware, software (including portable software, such as applets), firmware, or combinations thereof. Further, connection to other computing devices such as network input/output devices may be employed. Module terminal system 600 itself can be of varying types including a computer terminal, a personal computer, a portable computer, a workstation, a network computer, or any other data processing system. Due to the ever-changing nature of computers and networks, the description of module system 600 depicted in FIG. 4 is intended only as a specific example for purposes of illustrating one or more embodiments of the present disclosure. Many other configurations of module system 600 are possible having more or less components than the module system depicted in FIG. 4. Any of the modules or components of module system 600, or any combinations of such modules or components, can be coupled with, or integrated into, or otherwise configured to be in connectivity with, any of the cellular analysis system embodiments disclosed herein. Relatedly, any of the hardware and software components discussed above can be integrated with or configured to interface with other medical assessment or treatment systems used at other locations.

In some embodiments, the module system 600 can be configured to receive one or more cellular analysis parameters of a patient at an input module. Cellular analysis parameter data can be transmitted to an assessment module where raw sensor data or partially analyzed sensor data is further processed and/or evaluated in conjunction with additional information, possibly including prior laboratory results for the same patient; laboratory results from other types of analyzers or laboratory analyses; non-laboratory data about the patient, such as patient complaints, diagnostic history, vitals, or physical examination findings, or combinations thereof. The cellular analysis, such as WBC, MDW, NNRBC UMALS standard deviation, and other cell population parameters can be output to a system user via an output module. In some cases, the module system 600 can determine an initial treatment or induction protocol for the patient, or an adjusted treatment protocol, based on one or more cellular analysis parameters and/or the predicted sepsis status, for example by using a treatment module. The treatment can be output to a system user via an output module. Optionally, certain aspects of the treatment can be determined by an output device, and transmitted to a treatment system or a sub-device of a treatment system. Any of a variety of data related to the patient can be input into the module system, including age, weight, sex, treatment history, medical history, and the like. Parameters of treatment regimens or diagnostic evaluations can be determined based on such data.

Analysis system 304 of transducer module 300 or other code programs 618 of module system 600 or both may comprise one or more algorithms for processing sensor data generated by transducer module 300. The one or more algorithms may process the sensor data to identify and count cells. For example, individual cells may be identifiable based on light scatter and/or light transmission data that provides an indication of the size and certain surface properties of the cells. As another example, electrical impedance may provide an indication of the size of the cell. Radiofrequency conductivity may provide an indication of cellular constituents that may be useful in distinguishing granulocytes and nucleated versus non-nucleated cells. Markers, stains, image analysis or other measurement techniques may be used to identify cells as, for example, NNRBC, WBC, monocytes, neutrophils, and the like. An algorithm may count the number of signals consistent with a given cell type during an interrogation period, which may be defined by time through a flowcell or imaging time, or may be defined by a volume of body fluid examined, or both.

In some instances, the signals produced are continuous or ordinal values, and the magnitude or other properties of the signals may be further analyzed. For example, higher electrical impedance values typically indicate a larger cell, and may be useful for identifying a particular cell. Electrical impedance values may also correlate to cell volume, and therefore the magnitude of the signals across many cells in the sample may also convey useful information about that sub-population of cells. For example, electrical impedance values may help identify monocytes and distribution features of the volumes for the monocytes as a sub-population of cells may convey information about an immune response to an infection.

Figure 7:
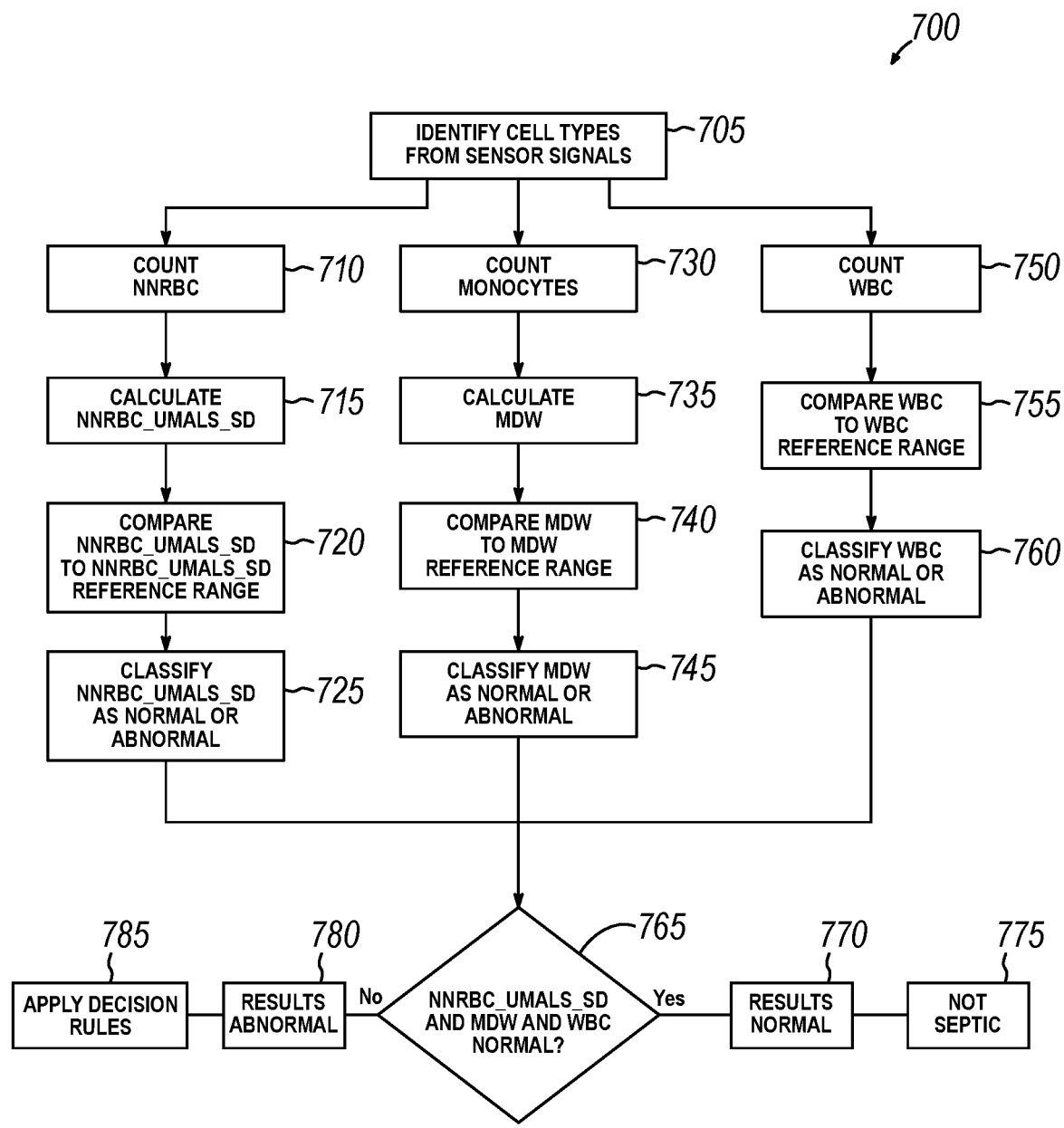
FIG. 7 is a flowchart of exemplary possible algorithms in accordance with aspects of this disclosure.

FIG. 7 is a flowchart for exemplary algorithms of potential use in practice of this disclosure. As shown, a single algorithm 700 encompasses all of the illustrated acts, however, different algorithms or even different software could be used, and, in particular, various acts could be performed by different algorithms or different software that might reside on or be processed by different hardware. Algorithm 700 may identify cell types from sensor signals 705. Algorithm 700 may count NNRBC 710. Algorithm 700 may calculate NNRBC-UMALS-SD 715. Algorithm 700 may compare the calculated NNRBC-UMALS-SD to an NNRBC-UMALS-SD reference range 720. Algorithm 700 may classify the NNRBC-UMALS-SD as normal or abnormal in relation to the NNRBC-UMALS-SD reference range 725.

Algorithm 700 may count monocytes 730. Algorithm 700 may calculate MDW 735. Algorithm 700 may compare the calculated MDW to an MDW reference range 740. Algorithm 700 may classify MDW as normal or abnormal in relation to the MDW reference range 745.

Algorithm 700 may count white blood cells 750. Algorithm 700 may compare the white blood cell count to a WBC reference range 755. Algorithm 700 may classify the WBC as normal or abnormal in relation to the WBC reference range 760.

Algorithm 700 may determine whether NNRBC-UMALS-SD, MDW and WBC are all normal in relation to their respective reference ranges 765. If yes, for this purpose the results are normal 770, and the patient is not identified as septic 775. If one or more of NNRBC-UMALS-SD, MDW and WBC are abnormal in relation to their respective reference ranges, then for this purpose the results are abnormal 780, and the algorithm may apply a global or local decision rules 785. A global decision rule is a threshold applied uniformly to all data processed by algorithm 700. In contrast, local decision rules may be permitted to allow different institutions or different practitioners to establish different rules for identifying a patient as having an abnormal immune response to infection, or for identifying a patient as being septic or at elevated risk of developing sepsis. Local decision rules allow institutions to adapt the specificity (ability to inclusively identify most or all cases of possible sepsis) and sensitivity (ability to exclude most or call non-sepsis cases) of the algorithm, to reduce false negatives or false positives, respectively. In most or all cases, it is contemplated that if all of NNRBC-UMALS-SD, MDW and WBC are abnormal, the results would be flagged as abnormal, and, if the results are used to identify sepsis, the patient would be identified as having sepsis or an elevated risk of developing sepsis. If the results are not all-normal or all-abnormal, the decision rules would apply either outcome A or outcome B in each row of the table below.

| NNRBC-UMALS-SD | MDW | WBC | Identify results overall as abnormal? |
|---|---|---|---|
| Normal | Not considered | Not considered | No |
| Normal | Not considered | Normal | No |
| Normal | Normal | Not considered | No |
| Normal | Normal | Normal | No |
| Normal | Not considered | Abnormal | A - No<br>B - Yes |
| Normal | Abnormal | Not considered | A - No<br>B - Yes |

| NNRBC-UMALS-SD | MDW | WBC | Identify results overall as abnormal? |
|---|---|---|---|
| Abnormal | Not considered | Not considered | Yes |
| Abnormal | Not considered | Abnormal | Yes |
| Abnormal | Abnormal | Not considered | Yes |
| Abnormal | Normal | Not considered | A - No<br>B - Yes |
| Abnormal | Not considered | Normal | A - No<br>B - Yes |
| Abnormal | Normal | Normal | A - No<br>B - Yes |
| Abnormal | Abnormal | Abnormal | Yes |

If the overall results are identified by algorithm 700 as abnormal, this may be presented as a separate analytical result (e.g., Sepsis Indicated? Yes/No), or may be presented as a flag to invite review by laboratory personnel and/or a clinician (e.g., text or other symbols or indicators in a report indicating that results indicate abnormal immune response to infection and/or indicate possible sepsis). Of course, in some instances, algorithm 700 may not apply any decision rules, deferring to laboratory and/or clinical personnel to interpret the results of the cellular analysis.

Figure 5:
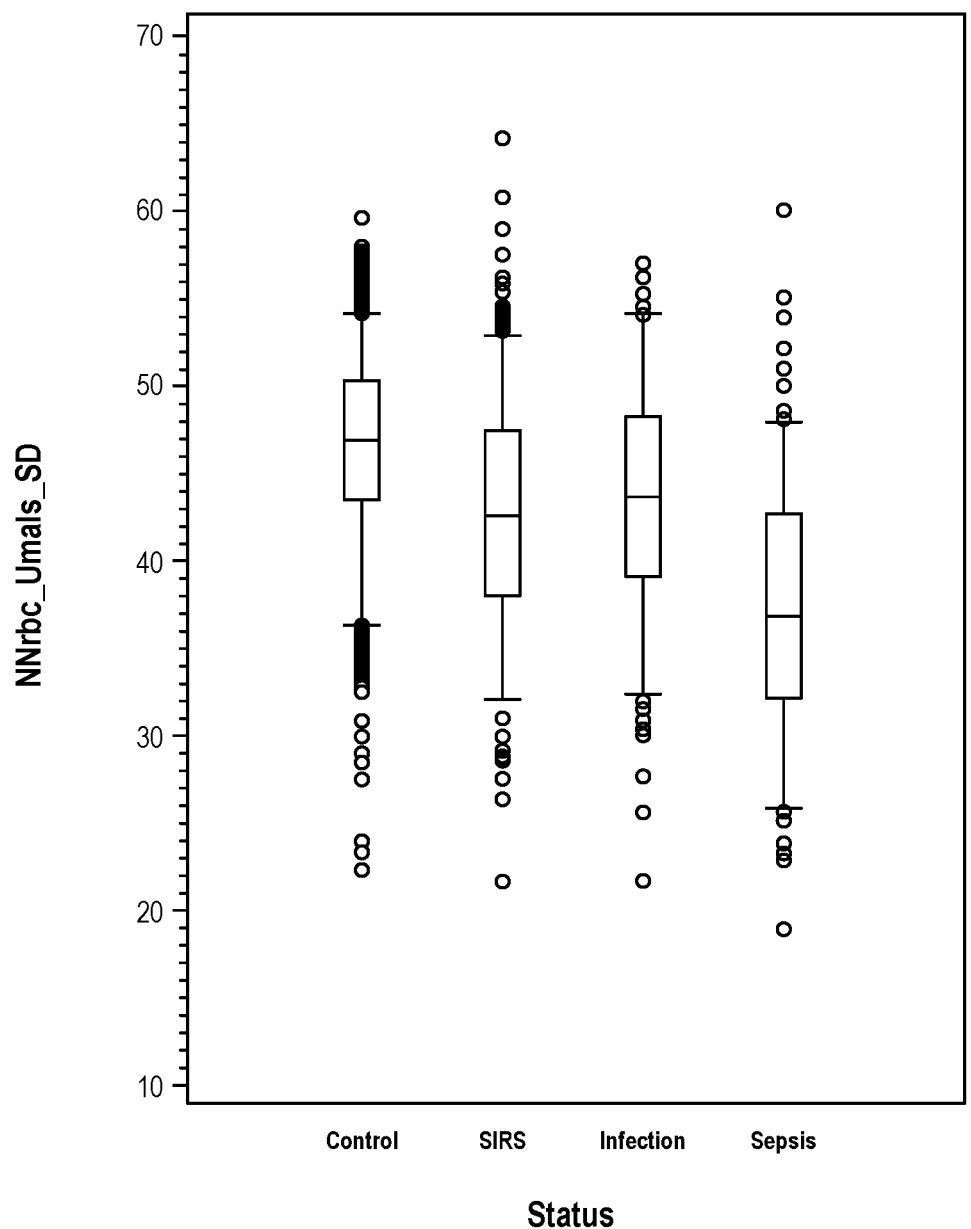
FIG. 5 is a Box Plot of NNRBC UMALS standard deviation by patient condition from an exemplary patient data set in accordance with aspects of this disclosure.

As noted above, a relatively new use of cellular analysis is the evaluation of the likelihood that a patient has or is at elevated risk (relative to a healthy person of similar age) of developing sepsis in the near-term (1 week or less). Such evaluation has so far centered on white blood cells or sub-populations of white blood cells, such as monocytes or immature granulocytes. However, the inventors have surprisingly found that the standard deviation of UMALS measurements for NNRBC (NNRBC-UMALS-SD) may also be predictive of sepsis. As shown in FIG. 5, NNRBC-UMALS-SD is markedly different in sepsis patients compared to healthy patients, and is distinguishable from patients who have Systemic Inflammatory Response Syndrome (SIRS) or Infection but not sepsis.

Figure 6:
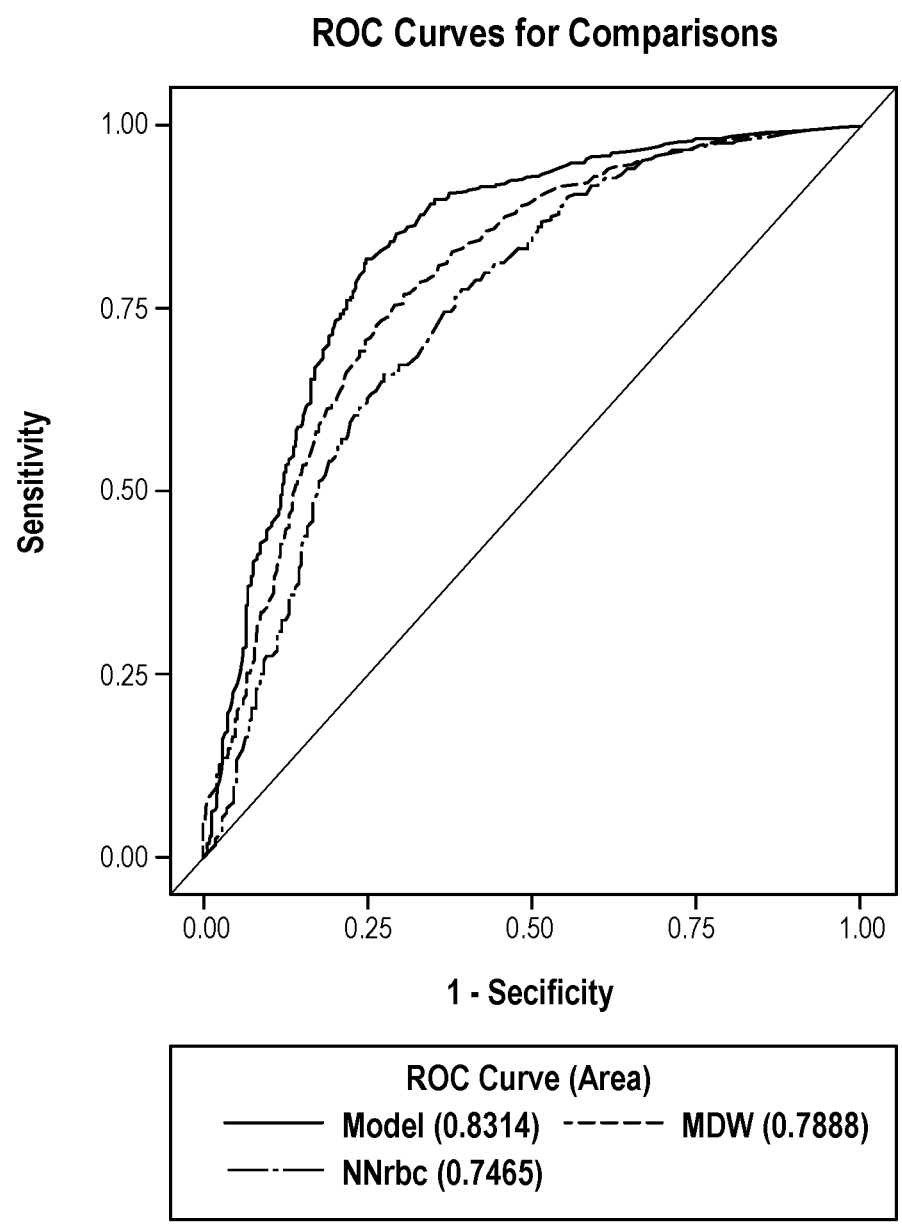
FIG. 6 is a ROC Curve with plots of sensitivity versus specificity for sepsis for NNRBC UMALS SD, MDW, and a combination of NNRBC UMALS SD and MDW in accordance with aspects of this disclosure.

FIG. 6 is an AUC-ROC curve, showing the relationships between MDW, NNRBC-UMALS-SD, and a model in which MDW and NNRBC-UMALS-SD are each compared to a threshold value for evaluating a patient's sepsis status. Based on this data set, as described further below, the model combining MDW and NNRBC-UMALS-SD should be able to correctly distinguish sepsis from other conditions approximately 83% of the time. This analysis, as with FIG. 5, comes from data collected in a pivotal clinical trial involving adult patients, 18-89 yrs., with complete blood count with differential performed upon presentation to the ED, and who remained hospitalized for at least 12 hours. A total of 2,158 subjects were enrolled and categorized per Sepsis-2 criteria: controls (n=1,088), systemic inflammatory response syndrome (SIRS) (n=441), infection (n=244), sepsis (n=385); and Sepsis-3 criteria: control (n=1,529), infection (n=386), sepsis (n=243).

The best of the inventors' knowledge, no prior study has looked at light scatter parameter changes for a heterogeneous cell population of circulating cells from a septic population, such as NNRBC, compared to controls. Prior studies have used hematological analyzers to look at light scatter changes in specific cell types during sepsis such as in specific lymphocyte, monocyte, or neutrophil cell populations (reviewed in Zonneveld R, Molema G, Plotz FB: Analyzing neutrophil morphology, mechanics, and motility in sepsis: options and challenges for novel bedside technologies. Crit Care Med 2016; 44: 218-228). With regard to cell surface granulation, no hypothesis-driven study has demonstrated a specific correlation between sepsis and cell surface granulation in any cell type.

It is well documented that sepsis causes a number of changes in circulating cells. Without wishing to be bound by theory, changes in membrane protein and lipid composition, changes in Na/Cl pump concentration, changes in ratios of cell types, and changes in the activation state of immune cells could be an underlying cause of a cellular granularity change that could impact light scattering. Any of these underlying biological mechanisms or combinations thereof could drive the observed light scatter differences in the NNRBC parameter. Nonetheless, obtaining the light scatter measurement and calculating particular cell population parameters, such as NNRBC-UMALS-SD, involve processes that would not occur in nature. The inventors have no indication that human-conducted visual examination of NNRBC granularity, e.g., via review of blood smear slides, would be useful in distinguishing septic and non-septic patients. Granularity can be assessed via blood smear review, but it is subjective and not standardized. Standard deviations cannot be visually assessed. In this study, mean NNRBC UMALS measurement was not as effective in identifying septic patients as NNRBC-UMALS-SD, suggesting that a human impression or estimate of granularity across a relatively small sample of cells would be unreliable for this purpose.

In some instances, an NNRBC-UMALS-SD reference range may be equal to or greater than 45, or equal to or greater than 43, or equal to or greater than 41.74, or equal to or greater than 41.5, or equal to or greater than 40, where values below these thresholds may be considered abnormal, associated with abnormal immune response to infection, and/or indicative of sepsis or elevated risk of sepsis. In some instances, NNRBC-UMALS-SD may be considered alongside one or more other parameters, such as WBC or MDW. For MDW, a value above 19, or above 20, or above 21, may indicated that a patient is septic or at elevated risk of developing sepsis. MDW may be measured in "channels" based on the signals collected to determine the volume of the monocytes. Of course, if monocyte volume distribution width is measured differently, as by image analysis, both the units and the normal range may vary. For WBC, a value below 4,000 cells/mm$^3$ or above 12,000 cells/mm$^3$ may indicate that a patient is septic or at elevated risk of developing sepsis. One of skill in the art will appreciate that these ranges are exemplary, and may vary based on the specific measurement methodologies used, as well as the specific hardware (e.g., light source, sensing hardware) used to make the measurements. In some instances, not only the reference range but also the unit of measure for these parameters may change based on the transducer module design used. Using two or more of these three criteria may increase the sensitivity and/or specificity of the cellular analysis for sepsis prediction relative to using only one of these three criteria.

NNRBC-UMALS-SD, alone or in combination with other cellular analyses, may be used in conjunction with current standard of care, including assessments like qSOFA and physical examination by a clinician (looking, e.g., for fever, altered mental state, tachycardia, tachypnea, hypotension, or other symptoms that may be undetectable or unreliably detectable from cellular analysis, blood chemistry, immunoassay, or other laboratory tests). Using the "Sepsis-2" consensus definition, the standard of care would include assessment of the patient for SIRS. A patient is considered to have SIRS when two or more of the following criteria are met: a temperature greater than 38 degrees Celsius (C) or less than 36 degrees C., a heart rate greater than 90 beats per minute (bpm), a respiratory rate greater than 20 breaths per minute (breaths/min), and a white blood cell count (WBC) less than 4,000 per microliter of blood (4,000/mm3) (leukopenia) or greater than 12,000/mm3 (leukocytosis). Under Sepsis-2, a patient is considered septic if the patient meets a minimum of 2 SIRS criteria plus a persistent infection (bacterial, viral or fungal). Using the "Sepsis-3" consensus definition, the standard of care would include a Sequential Organ Failure Assessment (SOFA) or a Quick SOFA (qSOFA). A qSOFA is scored on a scale from 0-3 points, with 1 point for each symptom that tests positively. These symptoms are a respiratory rate of over 22 breaths/min, systolic arterial blood pressure of less than or equal to 100 mmHg, and an altered mental status. It has been determined that patients with a qSOFA score of at least 2 have a 24% in-hospital mortality rate, and 3% for patents with a qSOFA score of less than 2. Typically, if the qSOFA score is of at least 2, then the patent will be evaluated with the full SOFA test. The SOFA test is scored on a scale of 0-24 and involves evaluating specific organ systems (respiratory, cardiovascular, liver, renal, coagulation, and central nervous system). If the SOFA score is also greater than or equal to 2 and has or is suspected of having an infection, then the patient is considered septic under Sepsis-3. In some aspects NNRBC-UMALS-SD may be used with or without other cellular analysis parameters, such as WBC and/or MDW, to provide additional insight into a patient's sepsis status when the standard of care does not result in a clear diagnosis. For example, under the Sepsis-2 criteria, an inability to definitively identify an infection, e.g., using blood culture, or an inability to wait for testing to confirm infection, e.g., if the patient's condition is too tenuous to wait several days for blood culture results, NNRBC-UMALS-SD may give a clinician confidence in initiating prophylactic treatment or heightened patient monitoring (such as in-patient admission for professional monitoring) by affirming other indicators of sepsis or developing sepsis.

The dimensions and values disclosed herein are not to be understood as being strictly limited to the exact numerical values recited. Instead, unless otherwise specified, each such dimension is intended to mean both the recited value and a functionally equivalent range surrounding that value to include at least the variability due to the reproducibility of measurements made using the test methods described herein, or industry-standard test methods if no test method is expressly disclosed.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

When used in the claims, the phrase "means for detecting whether a differentially expressed sepsis cell population parameter is present in a heterogenous population of circulating cells and characterizing an inflammatory response to infection based at least in part on that detection" should be understood as a means plus function limitation as provided for in 35 U.S.C. § 112(f), in which the functions "detecting whether a differentially expressed sepsis cell population parameter is present in a heterogenous population of circulating cells" and "characterizing an inflammatory response to infection based at least in part on that detection" are both recited, in which the corresponding structure for the first function is a computer configured to perform acts as illustrated with reference numbers 710-760 and described in the corresponding text, and the corresponding structure for the second function is a computer configured to perform acts as illustrated with reference numbers 765-785 and described in the corresponding text.

When used in the claims, the phrase "means for measuring RF conductivity" should be understood as a means plus function limitation as provided for in 35 U.S.C. § 112(f), in which the function is measuring RF conductivity, and the corresponding structure is electrodes as illustrated with reference numbers 334 and 336 and described in the corresponding text.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A system for characterizing an inflammatory response to infection, the system comprising:
   a. a transducer module configured to measure at least a cell granularity parameter of cells passing through a flowcell; and
   b. a processor configured with instructions stored on a non-transitory computer readable medium and operable to, when executed and based on measurement data from the transducer module, detect whether a differentially expressed sepsis cell population parameter is present in a heterogenous population of circulating cells passing through the flowcell by performing steps comprising:
      i. identifying one or more cells among the heterogenous population of circulating cells passing through the flowcell;
      ii. obtaining a plurality of measurements, wherein the plurality of measurements comprises, for the one or more cells a measurement of the cell granularity parameter; and
      iii. calculating a standard deviation of the measurements of the cell granularity parameter for the one or more cells.

2. The system of claim 1, wherein the processor is further configured to compare the standard deviation of the measurements of the cell granularity parameter for the one or more cells to a reference range.

3. The system of claim 2, wherein the processor is further configured to characterize the inflammatory response to infection as abnormal if the standard deviation of the measurements of the cell granularity parameter for the one or more cells is outside the reference range.

4. The system of claim 2, wherein the processor is further configured to identify and measure a volume of monocytes among the heterogenous population of circulating cells passing through the flowcell and calculate a distribution width of the monocyte volume measurements.

5. The system of claim 4, wherein the processor is further configured to compare the distribution width of the monocyte volume measurements to a second reference range, and to characterize the inflammatory response to infection as abnormal if the standard deviation of the measurements of the cell granularity parameter for the one or more cells is outside reference range and the distribution width of the monocyte volume measurements is outside the second reference range.

6. The system of claim 4, wherein the processor is further configured to determine a count of white blood cells among the heterogenous population of circulating cells passing through the flow cell.

7. The system of claim 6, wherein the processor is further configured to:
   a. compare the standard deviation of the measurements of the cell granularity parameter for the one or more cells to the reference range;
   b. compare the distribution width of the monocyte volume measurements to an second reference range;
   C. compare the count of white blood cells to a third reference range; and
   d. characterize the inflammatory response to infection based on a combination of at least the standard deviation of the measurements of the cell granularity parameter for the one or more cells, the distribution width of the monocyte volume measurements, and the count of white blood cells.

8. The system of claim 7, wherein the processor is configured to characterize the inflammatory response to infection as abnormal if the standard deviation of the measurements of the cell granularity parameter for the one or more cells is outside the reference range, the distribution width of the monocyte volume measurements is outside the second reference range and the count of white blood cells is outside the third reference range.

9. The system of claim 7, wherein the processor is configured to apply local decision rules to characterize the inflammatory response to infection if the standard deviation of the measurements of the cell granularity parameter for the one or more cells, the distribution width of the monocyte volume measurements and the count of white blood cells are not all within or all outside of their respective reference ranges.

10. The system of claim 1, wherein the one or more cells are classified as non-nucleated red blood cells.

* * * * *